United States Patent [19]
Sheppard et al.

[11] Patent Number: 5,817,324
[45] Date of Patent: Oct. 6, 1998

[54] USE OF ARYLPYRROLES FOR THE CONTROL OF RESISTANT INSECT POPULATIONS

[75] Inventors: David Craig Sheppard, Tifton, Ga.; Kathleen Heaney, Mercer County; Mary E. Doscher, Trenton, both of N.J.

[73] Assignee: American Cyanamid Company, Madison, N.J.

[21] Appl. No.: 840,785

[22] Filed: Apr. 16, 1997

[51] Int. Cl.$^6$ .............................. A61K 9/14; A01N 43/36
[52] U.S. Cl. ......................... 424/405; 424/489; 514/422
[58] Field of Search .................................. 424/405, 408, 424/409, 410, 411, 489, 438

[56] References Cited

U.S. PATENT DOCUMENTS 5,362,746  11/1994  Kameswaran et al. .................. 514/424
5,455,263  10/1995  Doscher et al. ........................ 514/422

OTHER PUBLICATIONS

Thomas, J.D., et al., *Pesticide Science*, 40(3): 239–243 (1994).
Brown, et. al., Abstract of Paper, American Chemical Society 205th Meeting, Part 1, AGRO 32, 1993.
Pimprale, S.S. and Brown, T.M., Abstract of Paper, American Chemical Society 206th Meeting, Part 1 AGRO 68, 1993.
Sheppard, D.C. and Hinkle, N.C., Journal of Agricultural Entomology, 41(1): 87–89 (Jan. 1987).
Scott, J.A., Florida Entomologist, 78(3): 399–409 (Sep. 1995).
Cilek, J.E. and Knapp, F.W., Journal of Agricultural Entomology, 3(3): 201–206 (Jul. 1986).
Levot, G.W. and Hughes, P.B., Journal of the Australian Entomological Society, 29: 257–259 (1990).
Daum, R.J., Bulletin of the Entomology Society of America, 16(1):10–1 (1970).
Sheppard, D.C. and Joyce, J.A., Journal of Economic Entomology, 85:1587–1593 (1992).
"The Pesticide Manual" 1994, British Crop Protection Council, XP002034019 Tenth Edition, pp. 7–8.

*Primary Examiner*—Thurman K. Page
*Assistant Examiner*—James M. Spear
*Attorney, Agent, or Firm*—John W. Hogan, Jr.

[57] ABSTRACT

There is provided a method for the control of pyrethroid-resistant insects and the protection of animals therefrom which comprises contacting said insects with a toxic amount of a formula I arylpyrrole compound.

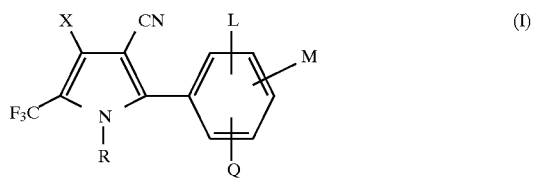

(I)

18 Claims, No Drawings

USE OF ARYLPYRROLES FOR THE CONTROL OF RESISTANT INSECT POPULATIONS

This application claims priority from provisional application 60/016,264 filed Apr. 19, 1996, now abandoned.

BACKGROUND OF THE INVENTION

Virtually all commercial and most companion animals are affected by parasites. The outcome associated with parasitism in said animals is generally clinical disease and subclinical conditions that decrease performance. Insects, such as Diptera (flies) and Phthiraptera (lice), are among the most economically important parasites in animal production. Insects, such as Siphonáptera (fleas) are highly pestiferous to companion animals. Many insects, such as *Haematobia irritans* (Diptera: Muscidae), require only 1–4 weeks to complete a life cycle during periods of warm temperatures. In Southern climates, as many as 20 generations of insects may develop annually. This rapidity of regeneration enables insect populations to develop resistance to environmental toxins such as insecticides.

Although, numerous insecticides may control insects effectively, most require frequent application. As a result, the efficacy of the insecticides may be severely compromised by the development of resistant populations such as pyrethroid-resistant insects. Thus, a new group of insecticides with selective toxicity against pyrethroid-resistant insects would be most advantageous.

Therefore, it is an object of this invention to provide a unique and highly effective group of arylpyrrole compounds useful for the control of pyrethroid-resistant insect populations.

It is another object of this invention to provide a method to enhance the protection of animals from the infestation of pyrethroid-resistant insects.

It is a feature of this invention that the method of treatment of the pyrethroid-resistant population will lead to a reduction in the frequency of resistant genes and a concomitant increase in the proportion of pyrethroid-susceptible genes in that population.

These and other features and objects of the invention will become apparent from the detailed description set forth below.

SUMMARY OF THE INVENTION

The present invention provides a method for the control of pyrethroid-resistant insects which comprises contacting said insects, their habitat, breeding area or food supply with a toxic amount of an arylpyrrole compound of formula I

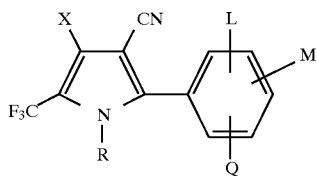

wherein R is hydrogen or $C_1$—$C_4$alkoxymethyl;
X is Cl or Br, and
L, M, and Q are each independently hydrogen, Cl, Br, I, F or $C_1$—$C_4$haloalkyl.

Also provided is a method for the enhanced protection of animals from the infestation of pyrethroid-resistant insects which comprises administering or applying to the animals an effective amount of a formula I arylpyrrole compound.

DETAILED DESCRIPTION OF THE INVENTION

Resistance is a widespread phenomenon and resistant populations of nearly all economically important pests can now be found. Insects highly resistant to pyrethroid insecticides pose a serious problem to animal health worldwide. Animal production and animal performance is greatly compromised by pyrethroid-resistant strains of insects, particularly of the orders Diptera (flies) and Phthiraptera (lice). Further, pyrethroid-resistant strains of Siphonáptera (fleas) can be a source of persistant annoyance to companion animals, as well as vectors of disease or intermediate hosts of certain tapeworms.

Resistance is herein defined as: a heritable reduction in the sensitivity of an insect population to the action of a pesticide, the reduction being expressed as a decrease in the frequency of individual insects affected by exposure to the pesticide (in comparison to the frequency observed in the same population upon initial or prior exposure).

A broad spectrum of arylpyrrole compounds are known to be useful for the control of endo- and ectoparasites on warm-blooded mammals (U.S. Pat. No. 5,455,263). However, it has now been found that the specific subset of arylpyrroles of formula I

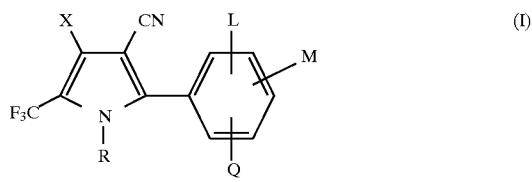

is highly efficacious against pyrethroid-resistant insects. Surprisingly, the formula I arylpyrroles are about 700%–1,100% more effective against pyrethroid-resistant insects than they are against pyrethroid-susceptible insects.

Important agronomic and companion animals such as cattle, sheep, horses, pigs, goats, water buffalo, deer, cats, dogs, rabbits, and the like are prone to attack and infestation by biting and sucking insects such as Diptera, Phthiraptera and Siphonáptera. In particular, Diptera: Muscidae such as *Musca autumnalis* (face flies), *Haematobia irritans* (horn flies), *Stomoxys calcitrans* (stable flies), heel flies, tsetse flies and the like are breeders of filth and vectors of disease and are serious pests of animals such as cattle, horses and sheep. Further, Diptera: Hippoboscidae (louse flies) such as *Melophagus ovinus* (sheep ked), which is a serious parasite of sheep are problematic in animal production.

Among the Phthiraptera families known to be parasites of animals are: Trichodectidae such as *Bovicola bovis* (important cattle-biting louse) or *B. equi* (horse-biting louse); Haematopinidae such as *Haematopinus suis* (hog louse), or *H. asini* (horse sucking louse); Linognathidae such as *Linognathus stenopsis* (goat sucking louse) or *L. vitali* (long-nosed cattle louse); and the like.

One of the Siphonáptera families known to infest companion animals is *Pulicinae* such as Archaeopsyllinae (cat and dog fleas), Spilopsyllinae (rabbit fleas), and the like.

Resistant insect populations may be detected and monitored readily by traditional methods such as bioassays or biochemical assays or by molecular techniques. Traditional bioassays, such as those described by Sheppard and Hinkle in J. Agric. Entomol. 4(1): 87–89 (1987), are able to detect the overall level of resistance present in a population in a single test.

Pyrethroid-resistant insects, particularly of the orders of Diptera, Phthiraptera, or Siphonaptera, more particularly of the families mentioned hereinabove, and most particularly of the species mentioned hereinabove may be effectively controlled by contacting said insects, their habitat, breeding area or food supply with a toxic amount of a formula I arylpyrrole compound. Preferred arylpyrrole compounds are those wherein X is Br and L, M and Q are each independently hydrogen or Cl. More preferred compounds are those wherein L and Q are hydrogen and M is 4-Chloro.

Among the formula I arylpyrrole compounds particularly useful in the method of the invention are:

4-bromo-2-(p-chlorophenyl)-1-(ethoxymethyl)-5-(trifluoromethyl)pyrrole-3-carbonitrile;
4-chloro-2-(p-chlorophenyl)-1-(ethoxymethyl)-5-(trifluoromethyl)pyrrole-3-carbonitrile;
4-bromo-2-(3,5-dichlorophenyl)-1-(ethoxymethyl)-5-(trifluoromethyl)pyrrole-3-carbonitrile;
4-bromo-2-(p-chlorophenyl)-5-(trifluoromethyl) -pyrrole-3-carbonitrile;
4-chloro-2-(p-chlorophenyl)-5-(trifluoromethyl) -pyrrole-3-carbonitrile;
4-bromo-2-(3,5-dichlorophenyl)-5-(trifluoromethyl) -pyrrole-3-carbonitrile; and the like.

Protection of animals from the infestation of pyrethroid-resistant insects, particularly of the orders Diptera, Phthiraptera and Siphonáptera, may be enhanced by the application or administration of an effective amount of an arylpyrrole compound of formula I. In actual practice, the formula I compound may be applied to the animal as a dip, spray, pour-on, backrubber, oiler, dustbag, powder, lotion or the like; or as an ear-tag or collar; or as an oral drench, bolus, pill, implant, capsule, feed or drinking water additive or the like; or as a parenteral injection; or the like.

The effective amount of the formula I arylpyrrole compound to be used in the method of invention will vary according to the specific compound used, the mode of application used, the identity of the pyrethroid-resistant insect to be controlled, the degree of infestation, the extent of the pyrethroid-resistant insect population, the nature of the target host, the weather conditions and the like. Effective dosages may range from about 0.1 mg/kg to 100 mg/kg, preferably about 1.0 mg/kg to 30 mg/kg. Naturally, quantities of greater than effective amounts of the arylpyrrole compound may be administered, but are not required for protection of the target animal from the pyrethroid-resistant insects.

In order to present a more clear understanding of the invention, the following specific examples are set forth below. These examples are merely illustrative and are not to be understood as limiting the scope and underlying principles of the invention in any way. Indeed, various modifications of the invention, in addition to those illustrated and described herein, will become apparent to persons skilled in the art from the following examples and the foregoing description. Such modifications are also intended to fall within the scope of the appended claims.

EXAMPLE 1

Evaluation Of The Effect Of Test Compounds vs. Cypermethrin On Susceptible And Resistant Strains Of Horn Flies (*Haematobia irritans*).

In this bioassay, highly pyrethroid-resistant wild flies and flies of a pyrethroid-susceptible lab strain are used. All flies are held in plastic petri dishes and exposed to sequential rates of test compound residue on filter paper[1]. A 1.25 inch hole is cut in the bottom half of the 100 mL petri dish and covered with fiberglass window screen. The bottom is used as the top in this bioassay, in order that the flies may be blood fed through the screened opening with a muslin pad saturated with citrated cattle blood.

The experiments are conducted in triplicate to determine 24 hour $LC_{50}$ data for the test compound and cypermethrin on susceptible and pyrethroid-resistant horn flies. The experiments are conducted on site so that freshly captured pyrethroid-resistant horn flies can be used. On the exemplified site, very high levels of pyrethroid resistance had been selected through several years of pyrethroid cattle ear tag use[2]. Wild pyrethroid-resistant horn flies are tested within 1 hour of capture to minimize check mortality. The resistance factor (RF) is determined by the following equation:

$$RF = \text{Resistant } LC_{50} \div \text{Susceptible } LC_{50}$$

The $LC_{50}$ is the concentration in $\mu g/cm^2$ of test compound required to kill 50% of the fly population tested. The $LC_{50}$ values are determined from the mortality data using standard log probit analysis techniques[3], and are within 95% confidence limits[1]. The data obtained is shown in Table I. The references listed below are incorporated herein by reference thereto.

TABLE I

| Exp.[4] | Test Compound | Susceptible $LC_{50}$ ($\mu g/cm^2$) | Resistant $LC_{50}$ ($\mu g/cm^2$) | RF |
|---|---|---|---|---|
| 1 | A | 1.2 | 0.356 | 0.30 |
|   | B | 0.122 | 79.02 | 640 |
| 2 | A | 2.15 | 0.294 | 0.14 |
|   | B | 0.057 | 65.20 | 1144 |
| 3 | A | 1.25 | 0.287 | 0.23 |
|   | B | 0.013 | 47.27 | 3636 |

Compound A = 4-Bromo-2-(p-chlorophenyl)-1-(ethoxymethyl)-5-(trifluoromethyl)pyrrole-3 -carbonitrile
Compound B = Cypermethrin
[1]Sheppard, D.C. and Hinkle, N.C., Journal Agricultural Entomology, 4, p. 87–89 (1987)
[2]Sheppard, D.C. and Joyce, J.A., Journal Economic Entomology, 85, p. 1587–1593 (1992)
[3]Daum, R.J., Bulletin of the Entomology Society of America, 16 (1): 10–12 (1970)
[4]Experiment

EXAMPLE 2

Evaluation Of Test Compounds vs. Permethrin On Susceptible And Resistant Strains Of Horn Flies (*Haematobia irritans*)

Using essentially the standard treated filterpaper-tarsal contact 24 hour bioassay described in Example 1, the following test compounds and pyrethroid insecticide are evaluated:

Compound A=4-Bromo-2-(p-cholorophenyl)-1-(ethoxymethyl)-5-(trifluoromethyl)pyrrole-3-carbonitrile
Compound C=4-Bromo-2-(p-chlorophenyl)-5-(trifluoromethyl)pyrrole-3-carbonitrile
Compound D=4-Chloro-2-(p-chlorophenyl)-1-(ethoxymethyl)-5-(trifluoromethyl)pyrrole-3-carbonitrile
Compound E=Permethrin The results are shown in Table II.

TABLE II

| Test Compound | Susceptible LC$_{50}$ ($\mu$g/cm$^2$) | Resistant LC$_{50}$ ($\mu$g/cm$^2$) | RF |
|---|---|---|---|
| A | 1.691 | 0.391 | 0.23 |
| C | 21.237 | 1.877 | 0.088 |
| D | 8.692 | 1.066 | 0.123 |
| E | 0.102 | 8.16 | 80.0 |

EXAMPLE 3

Evaluation Of Test Compound Activity Against Susceptible And Resistant Sheep Body Lice In this evaluation, test compounds are dissolved in acetone and diluted in a gradient series. One mL aliquots of the acetone dilutions are pipetted onto 6 cm cotton squares. The treated squares are dried and put into 9 cm petri dishes. Adult lice from the pyrethroid-susceptible Peak Hill strain and the pyrethroid-resitant Rowena strain are collected by suction from sheep, transferred onto each treated square and confined using a stainless steel ring (50 mm diameter×20 mm). After 16 hours, the lice are scored as dead, moribund or alive. In this bioassay, the test compound killed, rather than knocked-down lice. Each treatment is replicated. Standard log probit analysis techniques are used to determine the LC$_{50}$ and LC$_{99}$ values from the mortality data, and are within 95% confidence limits. The LC$_{50}$ values are then used to determine the resistance factor (RF) as shown below.

RF=Resistant LC$_{50}$÷Susceptible LC$_{50}$

The LC$_{50}$ is the concentration in mg/L of test compound required to kill 50% of the lice population tested. The LC$_{99}$ is the concentration in mg/L of test compound required to kill 99% of the lice population tested. The data are shown in Table III.

TABLE III

| Test Compound | Susceptible LC$_{50}$ (mg/L) | Resistant LC$_{50}$ (mg/L) | RF |
|---|---|---|---|
| 4-Bromo-2-(p-chlorophenyl)-1-(ethoxymethyl)-5-(trifluoromethyl-pyrrole-3-carbonitrile | 8.30 | 5.85 | 0.7048 |

| Test Compound | Susceptible LC$_{99}$ (mg/L) | Resistant LC$_{99}$ (mg/L) | |
|---|---|---|---|
| 4-Bromo-2-(p-chlorophenyl)-1-(ethoxymethyl)-5-(trifluoromethyl-pyrrole-3-carbonitrile | 52.8 | 24.5 | |

We claim:

1. A method for the control of pyrethroid-resistant insects selected from the group consisting of Trichodectidae, Haematopinidae, Linognathidae, Pulicidae, Muscidae, and Hippoboscidae which comprises contacting said insects, their habitat, breeding area, or food supply with a toxic amount of an arylpyrrole compound of formula I

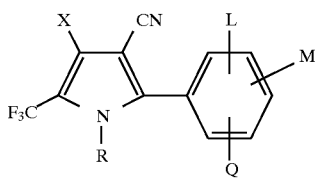

wherein R is hydrogen or C$_1$—C$_4$alkoxymethyl;

X is Cl or Br, and

L, M, and Q are each independently hydrogen, Cl, Br, I, F or C$_1$—C$_4$haloalkyl.

2. A method for enhancing the protection of animals from the infestation of pyrethroid-resistant insects selected from the group consisting of Trichodectidae, Haematopinidae, Linognathidae, Pulicidae, Muscidae, and Hippoboscidae which comprises administering or applying to the animals an effective amount of an arylpyrrole compound of formula I

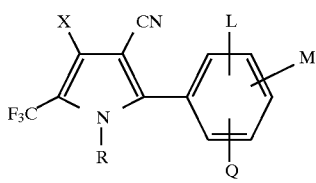

wherein R is hydrogen or C$_1$—C$_4$alkoxymethyl;

X is Cl or Br, and

L, M, and Q are each independently hydrogen, Cl, Br, I, F or C$_1$—C$_4$haloalkyl.

3. The method according to claim 1 wherein the Pyrethroid-resistant insects are Trichodectidae, Haematopinidae or Linognathidae.

4. The method according to claim 1 wherein the pyrethroid-resistant insects are *Pulicidae*.

5. The method according to claim 1 wherein the pyrethroid-resistant insecs are Muscidae or Hippoboscidae.

6. The method according to claim 5 wherein the Muscidae is *Haematobia irritans, Musca autumnalis*, or *Stomoxys calcitrans*.

7. The method according to claim 6 wherein the Muscidae is *Haematobia irritans*.

8. The method according to claim 1 wherein R is ethoxymethyl.

9. The method according to claim 8 wherein the arylpyrrole compound is 4-bromo-2-(p-chlorophenyl)-1-(ethoxymethyl)-5-(trifluoromethyl)pyrrole-3-carbonitrile or 4-chloro-2-(p-chlorophenyl)-1-(ethoxymethyl)-5-(trifluoromethyl)pyrrole-3-carbonitrile.

10. The method according to claim 1 wherein R is hydrogen.

11. The method according to claim 10 wherein the arylpyrrole compound is 4-bromo-2-(p-chlorophenyl)-5-(trifluoromethyl)pyrrole-3-carbonitrile.

12. The method according to claim 1 wherein L and Q are each hydrogen and M is 4-chloro.

13. The method according to claim 2 wherein R is ethoxymethyl.

14. The method according to claim 2 wherein the animals are cattle, sheep or buffalo.

15. The method according to claim 2 wherein R is hydrogen.

16. The method according to claim 2 wherein L and Q are each hydrogen and M is 4-chloro.

17. The method according to claim 13 wherein the arylpyrrole compound is 4-bromo-2-(p-chlorophenyl)-1-(ethoxymethyl)-5-(trifluoromethyl)pyrrole-3-carbonitrile or 4-chloro-2-(p-chlorophenyl)-1-(ethoxymethyl)-5-(trifluoromethyl)pyrrole-3-carbontrile.

18. The method according to claim 15 wherein the arylpyrrole compound is 4-bromo-2-(p-chlorophenyl)-5-(trifluoromethyl)pyrrole-3-carbonitrile.

* * * * *